(12) United States Patent
Handal Vega et al.

(10) Patent No.: US 6,870,057 B1
(45) Date of Patent: Mar. 22, 2005

(54) SYNTHESIS PROCEDURE FOR BIPHENYLIMIDAZOLYL-(1)-PHENYLMETHANE AND RELATED COMPOUNDS

(75) Inventors: Erlinda Handal Vega, San Salavador (SV); Carmen Elena Arias, La Paz (SV); Jorge Manuel Collazo Garcia, San Salvador (SV)

(73) Assignee: Manufacturas Humberto Bukele E Hijos, S.A. DE C.V., San Salvador (SV)

( * ) Notice: Subject to any disclaimer, the term of this patent is extended or adjusted under 35 U.S.C. 154(b) by 29 days.

(21) Appl. No.: 10/276,719

(22) PCT Filed: May 17, 2001

(86) PCT No.: PCT/IB01/01156
§ 371 (c)(1),
(2), (4) Date: Jul. 7, 2003

(87) PCT Pub. No.: WO01/87848
PCT Pub. Date: Nov. 22, 2001

(30) Foreign Application Priority Data

May 17, 2000 (SV) .................................... 012000000073

(51) Int. Cl.$^7$ .............................................. C07D 233/58
(52) U.S. Cl. .................................................. 548/344.1
(58) Field of Search ...................................... 548/344.1

(56) References Cited

U.S. PATENT DOCUMENTS 4,118,487 A   10/1978   Regel et al.

OTHER PUBLICATIONS

Federico Corelli, et al., "Chiral Azole Derivatives. 2. Synthsis of Enantiomerically Pure 1–Alkylimidazoles", Journal of Organic Chemistry., vol. 60, No. 7, (1995) pp. 2008–2015, XP002189742.

*Primary Examiner*—Laura L. Stockton
(74) *Attorney, Agent, or Firm*—Sughrue Mion, PLLC

(57) ABSTRACT

Synthesis of Bifonazole by reducing 4-phenylbenzophenone to the alcohol and reacting the alcohol in solid phase under microwave irradiation with imidazole.

15 Claims, 3 Drawing Sheets

SYNTHESIS PROCEDURE FOR BIPHENYLIMIDAZOLYL-(1)-PHENYLMETHANE AND RELATED COMPOUNDS

BACKGROUND

The instant invention is related to the synthesis of active principles of medicaments, specifically to the synthesis of antimycotics. Our method of synthesis consists of the manufacture of biphenylimidazolyl-(1)-phenylmethane, or (biphenyl-4yl)-imidazol-1-yl-phenylmethane, from 4-phenylbenzophenone (1). The method consists of two synthesis steps: the reduction of (I) to biphenylphenylcarbinol (II) and the subsequent addition of imidazole (III) to the alcohol produced. Both synthesis steps are fast and of easy execution; the whole synthesis process does not exceed three hours. Contrary to previous methods, it does not require the use of thionyl chloride, or solvent in the synthesis process. It yields between 70 to 74% biphenylimidazolyl-(1)-phenylmethane (IV).

Bifonazole, or (biphenyl-4-yl)-imidazol-1-yl-phenylmethane is a potent antimycotic, prepared for the first time by Bayer in 1974, patent granted in 1976 (Ger.Pat. 2,461,406). Since then, many modifications have been made to the same patent, all of which are registered by Bayer (U.S. Pat. No. 4,118,487).

The method of synthesis presented in Ger.Pat. 2,461,406 uses 4-phenylbenzophenone as partition reactant, and has 2 or three steps, depending on the variation of synthesis to use. One of the variations comprises the dissolution of 4-phenylbenzophenone in ethanol, then adding sodium borohydride in a 1:2 molar relation to 4-phenyl benzophenone, for the reduction of ketone to alcohol. The system is heated to reflux during fifteen hours, it is let to cool down and the reaction mixture is hydrolyzed with water acidulated with HCl, the solid obtained is purified by recrystallization in ethanol. 89% of the theoretical yield of biphenyl-phenyl-carbinol is obtained.

The second and third stage of synthesis consists of making imidazole react with thionyl chloride, using acetonitrile as solvent; the operation is performed at 10° C. To the resulting thionylbisimidazole solution, biphenylphenyl-carbinol is added in a 1:4 molar relation to the thionyl. After fifteen hours at room temperature, the solvent is removed by vacuum distillation. The remaining is dissolved in chloroform and washed with water, the organic phase is dried over sodium sulfate; after filtering, the solvent is vacuum distilled. The resulting solid is purified by recrystallization in acetonitrile. Bifonazole is obtained in 56% yield in relation to the theoretical.

Another variant consists of making biphenylphenylchloromethane react (product chlorated from biphenyl-phenyl-carbinol), with n-trimethylsilylimidazole dissolved in acetonitrile. The system is heated at reflux during fifteen hours, then the solvent is distilled, the residue is purified by recrystallization in ethyl acetate. Bifonazole is obtained in 56% yield in relation to the theoretical.

The German Patent 3,538,873 (1987) describes a method of synthesis for several molecules with antimycotic properties, among them Bifonazole; reacting 4-benzoylbiphenyl with imidazole in a 1:4 molar relation in p-$CH_3C_6H_4SO_3H$; heating the system at 180 degrees Celsius; then adding formic acid dropwise during five hours. A mixture of water-formic acid is distilled at the end of the reaction. Bifonazole is obtained in a 72.3% yield in relation to the theoretical.

Other methods use dichloromethane as solvent and add triethylamine making react biphenylphenylchloromethane with n-trimethylsilylimidazole at reflux during 5 to 10 hours; or forming n-trimethylsilylimidazole "in situ" from imidazole and $CH_3SiCl$ (Es. Patent 531,107).

Another preparation starts from cyciocondensation of 4-$PhC_6H_4CHPhNH_2$, $ClCH_2CH_2NH_2HCl$ and $HC(OEt)_3$ in the presence of a proton acceptor in EtOH, followed by a dehydrogenation of the resulting (biphenylbenzyl) imidazoline, which was dehydrogenated with DDQ in benzene, to yield Bifonazole (Es. Patent 549,793), no yield reported.

Bifonazole has also been prepared by benzoylation of imidazole with PhCOCl, yielding 74.7% of 1-benzoylimidazole which is subject to react with Gringnard's reactant 4-$PhC_6H_4MgBr$ followed by a tosylation and subsequent reduction with sodium cyanoborohydride in hexamethylphosphoramide, to yield 68.2% Bifonazole (Es. Patent 539,345).

One can also start from imidazole, which is make to react with formic acid at 220° C. to obtain the amide; when cooling the system at 50° C., a mixture of 4-phenylbenzophenone is added in formic acid, and the system is heated at 200° C. during twenty hours, then it is stirred overnight with KOH, water and toluene to produce Bifonazole. No yield reported (East Germany DD 249.268).

SUMMARY OF THE INVENTION

Our method of synthesis for Bifonazole uses 4-phenylbenzophenone as a starting reactant, and it comprises two steps: the first one consists of the reduction of ketone to alcohol with sodium borohydride, and the second, of the reaction of biphenyl-phenyl-carbinol with imidazole.

The reduction is performed in the presence of alumina, using a small amount of ethanol or other protic solvent, just enough to form a kind of paste with alumina, sodium borohydride and 4-phenylbenzophenone in a container adapted to a condenser; the reaction is strongly exothermic and does not need external heating; the reaction lasts from 10 to 60 minutes; then the product is hydrolyzed with water acidulated with HCl. The product is separated by filtration. A 99% conversion of (I) to (II) is obtained and 92–96% of (II) after recrystallization starting from ethanol, where the reduction of 4-phenyl-benzophenone is carried out in the presence of sodium borohydride in the presence of alumina and ethanol and the time of reaction is from 10 to 60 minutes, and the conversion of 4-phenyl-benzophenone into biphenyl-phenyl-carbinol is 90–99%.

The second step of synthesis is performed through a reaction in solid phase, in excess of imidazole. The mixture is heated in a microwave oven. The microwave energy used to carry out the solid phase reaction can be determined through routine experimentation, since it is easy to analyze for the Bifonazole product, with the exemplification set forth herein as guidelines. Microwave times of 3 to 40 minutes can often be used. For example, for a sample weight of about 0.75 g, the sample can be placed in a conventional microwave oven rated at 850 watts at about 22–25 cm from the Magnetron with the microwave run at 30 to 50% power for about 30 minutes. The product is recrystallized from acetonitrile. 70 to 74% of the theoretical yield (pure product) is obtained in relation to the initial amount of 4-phenylbenzophenone. The great advantages of this method are:

1. The use of thionyl chloride is not necessary.
2. The only organic solvents used are ethanol and acetonitrile, and they are used in small amounts.
3. The whole synthesis process lasts two hours.
4. High yields are obtained in each synthesis step.
5. The environment is not contaminated by using reactants such as thionyl chloride, or solvents such as benzene, hexamethylphosphoramide, triethylamine, or toluene.

The process of the present invention can be employed for production of other triphenyl imidazole methane derivatives, especially the second step of solid phase reaction under microwave energy, from the known triphenylimidazoyl carbinols whether produced by the carbinol-producing step herein or not.

DETAILED DESCRIPTION

In the practice of this invention, 1 to 0.05 moles of benzophenone can be reacted with 1.0 mole of borohydride; 0.01 to 25 mass units of the alumina can be used for 1.0 mass unit of the benzophenone; 1 to 2 mass units of the protic solvent can be used for 1.0 mass unit of the benzophenone; and the molar ratio of carbinol to imidazole can be 1:1–8. The reaction between biphenyl-phenyl carbinol and imidazole can be carried out in the absence of any organic or inorganic solvent.

EXAMPLE 1

Figure 1:
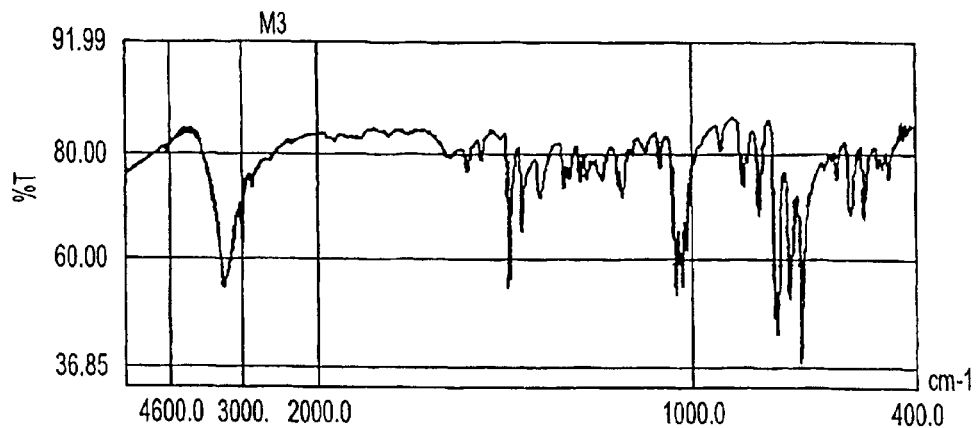
FIG. 1 is an infrared of spectrum obtained Biphenylphenylcarbinol under experimental conditions of Example No. 1.

First Synthesis step: 10.0 g ($3.87 \times 10^{-2}$ mole) of (I), were supported by chemisorbtion in 10.0 g of alumina using 20 mL ethanol until forming a paste (slightly humid), to which 1.5 g of sodium borohydride ($3.96 \times 10^{-2}$ mole) is added. The system is stirred by magnetic stirring during forty minutes at room temperature. This is performed in a container with a reflux system. Then acidulated water at pH1 was added to the system to hydrolyze excess of borohydride; the product with the alumina support was vacuum filtered in a Buchner; the support loaded with the reaction product is washed with water until neutral pH of the filtrate; then the loaded support is washed with ethanol at 70° C. with stirring. 99% conversion of (I) to (II) was obtained. The alumina is filtered and the filtrate is left to crystallize. 92% of the pure alcohol (II) was obtained. The products were analyzed by TLC (thin layer chromatography) and infrared spectroscopy See spectrum FT-IR in FIG. 1.

Figure 2:
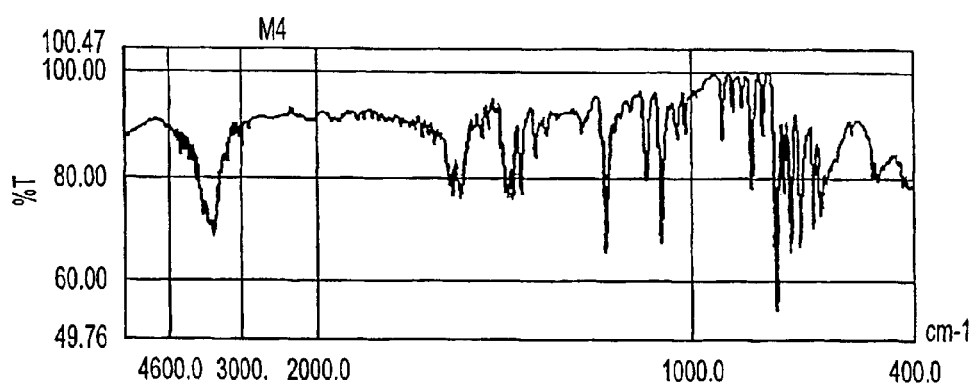
FIG. 2 is an infrared spectrum of obtained Bifonazole under experimental conditions of Example No. 1
Figure 3:
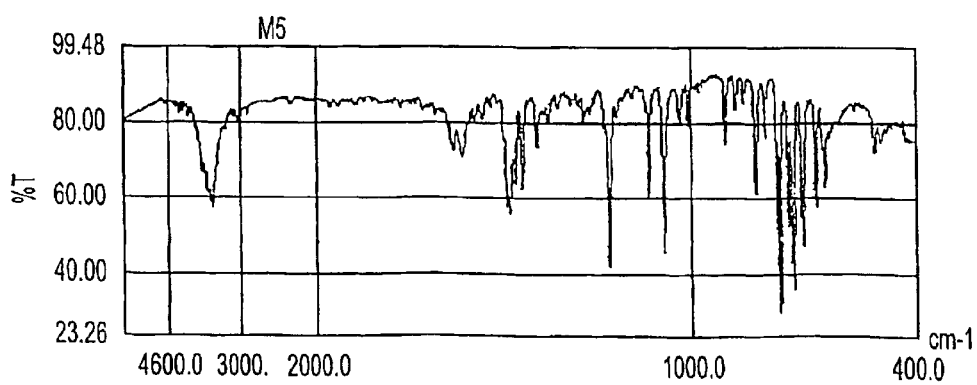
FIG. 3 is an infrared spectrum of Bifonazole of Laboratories Chile.
Figure 4:
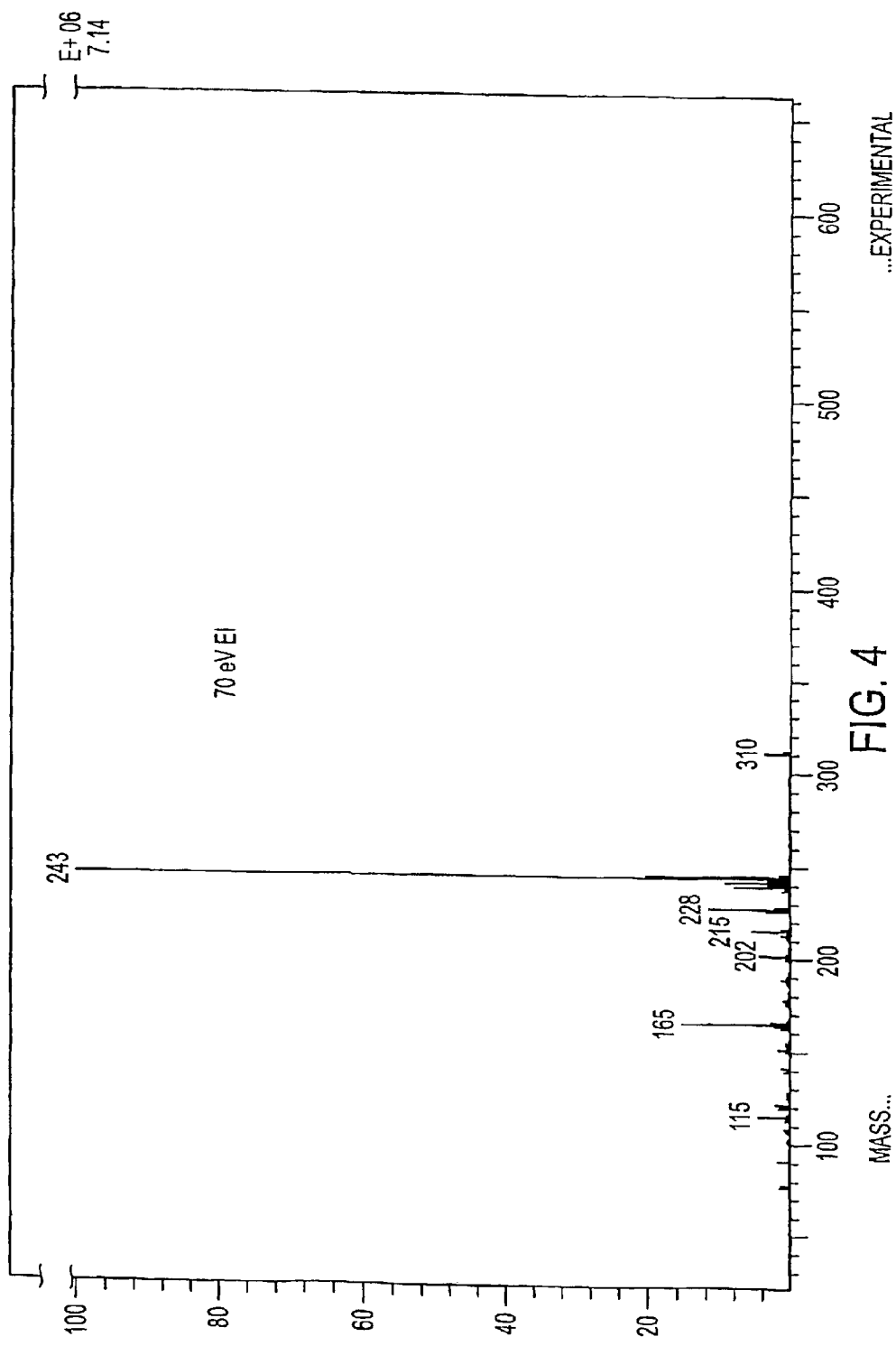
FIG. 4 is a mass spectrum of obtained Bifonazole under experimental conditions of Example No. 1.
Figure 5:
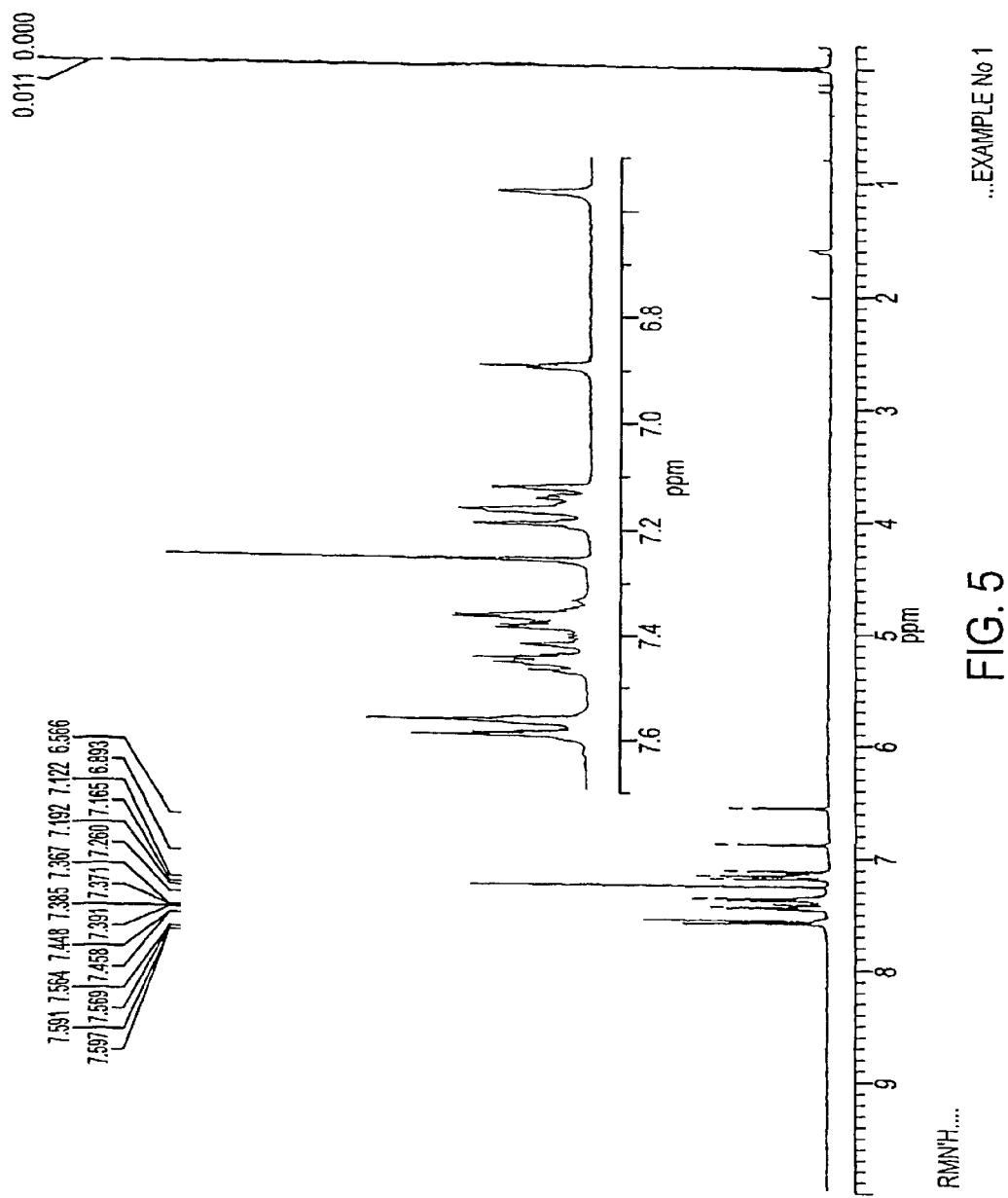
FIG. 5 is a NMR$^1$H spectrum of obtained Bifonazole under experimental conditions of Example No. 1.

Second step of synthesis: 0.2476 g ($9.9 \times 10hu 31\ 4$ mole) of (II) was mixed with 0.5246 g of (III) ($7,96 \times 10^{31\ 4}$ mole) in absence of solvent, placed in a sealed container, which was placed in a microwave oven (850 watts). The sample was irradiated during thirty minutes at 40 power, getting a reaction yield of 71.6% of (IV), or Bifonazole. Mass and MNR'H spectra of the recrystallized product (see FIG. 4 and 5) were obtained. The infrared spectrum of the product (FIG. 2) can be compared with a known (registered) IR (FIG. 3).

EXAMPLE 2

First step of synthesis: 93.2% of compound (II) was obtained according to the first step of synthesis of Example 1.

Second step of synthesis: 0.25 g ($9.6 \times 10^{-4}$ mole) of (II) was mixed with 0.5251 g, ($7.7 \times 10^{-3}$ mole) of (III) in absence of solvent, placed in a sealed container, which was placed in a microwave oven (850 w). It was irradiated during thirty minutes at 50 power. Reaction yield after recrystallization of the product was 72% of (IV).

EXAMPLE 3

First synthesis step: 96.3% of compound (II) was obtained according to the first step of synthesis of Example 1.

Second step of synthesis: 0.25 g, ($9.6 \times 10^{-4}$ mole) of (II) was mixed with 0.5252 g, ($7.7 \times 10^{-3}$ mole) of (III) in the absence of solvent, placed in a sealed container, which was placed in a microwave oven (850 W). It was irradiated during thirty minutes at 40 power. After recrystallization of the product the yield obtained was 73.9% of (IV).

Variations of the invention will be apparent to the skilled artisan.

What is claimed is:

1. A synthesis procedure for the manufacture of biphenylimidazolyl-(1)-phenylmethane, comprising the reduction of 4-phenyl-benzophenone and subsequent reaction of biphenyl-phenyl-carbinol with imidazole.

2. A synthesis procedure according to claim 1, where the reduction of 4-phenyl-benzophenone is carried out with sodium borohydride in the presence of alumina.

3. A synthesis procedure according to claim 1, where the molar ratio between 4-phenyl-benzophenone and sodium borohydride is 1:0.5 moles of the benzophenone to 1.0 mole borohydride (1:0.5-1).

4. A synthesis procedure according to claim 1, where the ratio in mass between alumina and 4-phenyl-benzophenone is 0.01:25-1.

5. A synthesis procedure according to claim 1, where a protic solvent is used, for example ethanol.

6. A synthesis procedure according to claim 1, where the protic solvent used is in a mass ratio with 4-phenyl-benzophenone of 1:2-1.

7. A synthesis procedure according to claim 1, where the time of reaction between sodium borohydride and 4-phenyl-benzophenone in the presence of alumina and ethanol is from 10 to 60 minutes.

8. A synthesis procedure according to claim 7, where no heating is necessary besides the exothermal effect produced by the reaction itself.

9. A synthesis procedure according to claim 8, where the conversion of 4-phenyl-benzophenone into biphenyl-phenyl-carbinol is 90–99%.

10. The synthesis procedure according to claim 1, where the carbinol reacts in a further step of synthesis with imidazole, in a molar ratio of carbinol to imidazole of 1-1:8.

11. A synthesis procedure according to claim 10, where the reaction between biphenyl-phenyl-carbinol and imidazole is carried out in the absence of any organic or inorganic solvent.

12. A synthesis procedure according to claim 11, where the reaction between biphenyl-phenyl-carbinol and imidazole is carried out by subjecting the system to microwave irradiation.

13. A synthesis procedure according to claim 12, where the reaction time is from 3 to 40 minutes.

14. A synthesis procedure according to claim 13, where biphenylimidazolyl-(1)-phenylmethane is obtained as a reaction product in a yield of 70 to 74% of pure product.

15. A synthesis procedure for the manufacture of biphenylimidazolyl-(1)phenylmethane starting from 4-phenyl-benzophenone, which consists of two synthesis steps, being the first one the reduction of 4-phenyl-benzophenone to biphenyl-phenyl-carbinol with sodium borohydride in the presence of alumina, and the second step consists of the reaction between biphenyl-phenyl-carbinol and imidazole assisted by microwaves, and in the absence of every kind of organic and inorganic solvents, obtaining a yield between 70 to 74% of pure product in a total reaction time of no more than three hours, starting from 4-phenyl-benzophone.

* * * * *